United States Patent
Banko et al.

(10) Patent No.: US 7,083,589 B2
(45) Date of Patent: Aug. 1, 2006

(54) ULTRASONIC INSTRUMENT WITH COUPLER FOR WORK TIP

(75) Inventors: William Banko, Mamaroneck, NY (US); Gordon D. Coplein, Dunwoody, GA (US)

(73) Assignee: Surgical Design Corporation, Armonk, NY (US)

( * ) Notice: Subject to any disclaimer, the term of this patent is extended or adjusted under 35 U.S.C. 154(b) by 470 days.

(21) Appl. No.: 10/013,397

(22) Filed: Dec. 11, 2001

(65) Prior Publication Data

US 2003/0114873 A1   Jun. 19, 2003

(51) Int. Cl.
  A61B 17/20  (2006.01)
  A61C 1/07  (2006.01)
  A61C 3/03  (2006.01)
  A61C 3/08  (2006.01)

(52) U.S. Cl. .................................. 604/22; 433/119

(58) Field of Classification Search ............ 604/19–22, 604/118, 169, 167, 264, 272; 606/169, 171, 606/167; 433/118–120
See application file for complete search history.

(56) References Cited

U.S. PATENT DOCUMENTS

| | | | | |
|---|---|---|---|---|
| 3,589,363 A | * | 6/1971 | Banko et al. ................. | 604/22 |
| 4,223,676 A | * | 9/1980 | Wuchinich et al. ........... | 604/22 |
| 4,504,264 A | * | 3/1985 | Kelman ....................... | 604/22 |
| 5,242,385 A | | 9/1993 | Strukel | |
| 5,776,155 A | * | 7/1998 | Beaupre et al. ............. | 606/169 |
| 5,827,292 A | * | 10/1998 | Anis .......................... | 606/107 |

* cited by examiner

Primary Examiner—Nicholas D. Lucchesi
Assistant Examiner—Matthew F. DeSanto
(74) Attorney, Agent, or Firm—Gordon D. Coplein

(57) ABSTRACT

An ultrasonic instrument includes generator of ultrasonic energy; a connecting body that receives ultrasonic energy from the generator and having an end from which the energy exits and a coupler at such end exterior of the connecting body having an inlet aspiration flow passage for receiving aspiration flow force from a source. A work tip has its proximal end connected to the coupler to receive the generated ultrasonic energy and a distal end from which the ultrasonic energy is supplied to the operating site to emulsify material. The work tip has an aspiration passage that is in communication with an aspiration passage in the coupler that communicates with the inlet passage and at least one of the work tip is detachable from the coupler and coupler detachable from the connecting body. Aspiration fluid flow force is provided through the coupler to the work tip aspiration passage without coming into contact with the interior of the connecting body to thereby permit removal of the work tip so that the instrument can be reused by replacing the work tip and without sterilization of the connecting body.

12 Claims, 4 Drawing Sheets

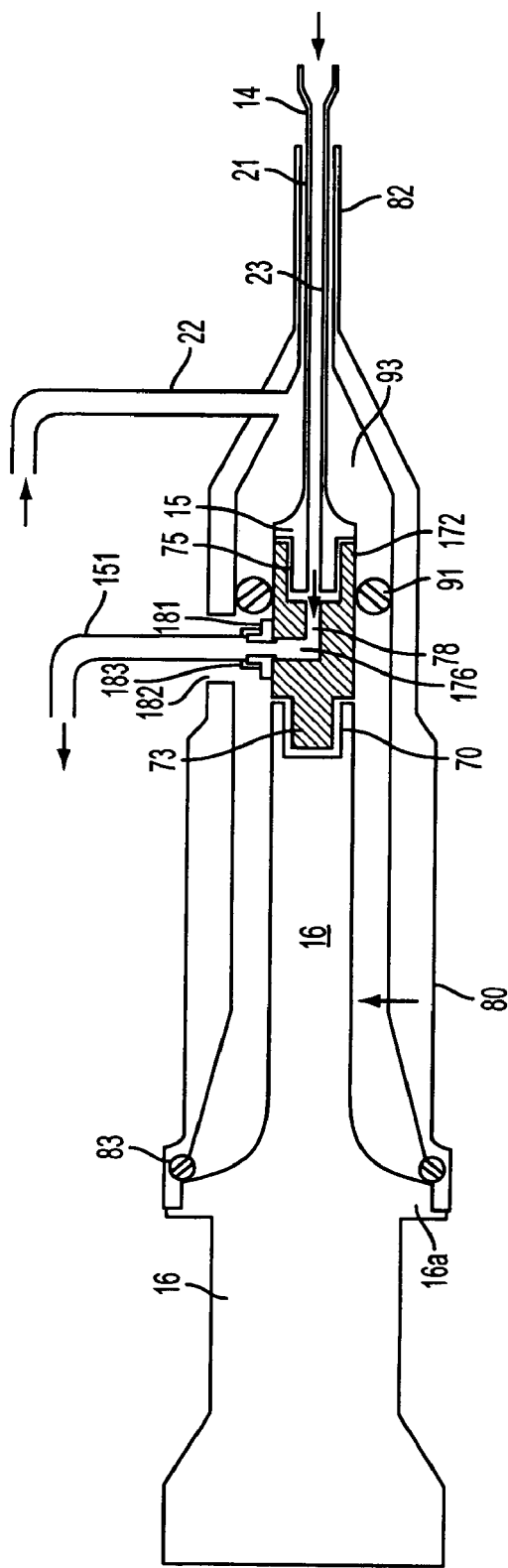
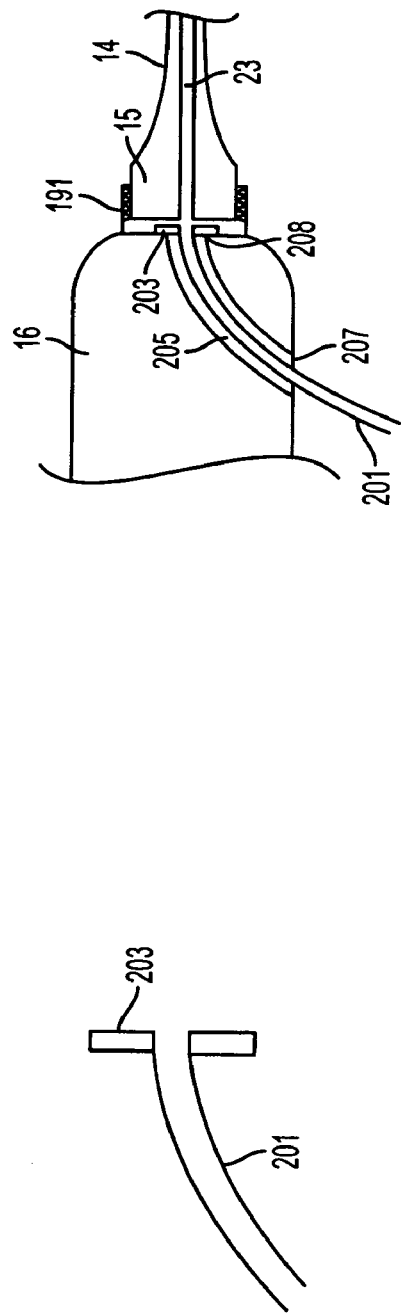
FIG. 4
FIG. 5
FIG. 5A

ULTRASONIC INSTRUMENT WITH COUPLER FOR WORK TIP

BACKGROUND OF THE INVENTION

The use of ultrasonic instruments in surgical applications is well known. One widely used type of instrument is an ultrasonic handpiece that is used in opthalmological applications, such as in the removal of cataracts from the eye. A typical instrument uses a magnetostrictive transducer formed by a stack of laminations surrounded by a coil of wire to which alternating current energy is applied. The stack of laminations converts the electrical energy to mechanical vibratory energy. A work tip is at the distal end of the handpiece that is connected to the transducer by a connecting body. The mechanical vibratory energy produced by the transducer is conveyed to the distal end of the work tip and this energy is applied close to or against a piece of tissue that is emulsified by the vibratory energy.

Such a handpiece usually utilizes a source of aspiration flow force so that the emulsified tissue can be removed from the operating site. The aspiration force can be provided by, for example, a peristaltic type suction pump and there is a fluid connection between the pump and the work tip, usually through a central aspiration passage formed in the work tip that is in communication with the aspiration force pump through a conduit that is connected to a fitting on the handpiece that is in communication with the tip central passage. The aspiration flow force passage also can extend through the connecting body. Hand pieces of this type can also have a sleeve, or cocoon, that surrounds and is spaced from the work tip to form a passage through which an irrigation fluid is supplied from an external source. The irrigation fluid exits from this passage at or near the distal end of the tip to supply the irrigation fluid to the operating site.

After each use, the complete handpiece can be sterilized, such as by a conventional gas sterilization technique, or the work tip alone can be immersed in a liquid sterilizing solution. In instruments of this type there often is a threaded connection between the proximal end of the work tip and the connecting body. The threaded connection is relatively permanent in the sense that it is broken only when the work tip has to be replaced, this occurring after many uses of the handpiece.

A need exists to provide an ultrasonic handpiece of the forgoing type in which the work tip would be used for only a single use and then disposed of. This can have a desired advantage of eliminating the need for sterilization of the handpiece, or making sterilization easier, and making conditions for use of the instrument more sanitary from one patient to the next. However, if the work tip is to be made for single use, it becomes necessary to provide an arrangement by which the tip can be easily changed and the aspiration and irrigation flow passages can be easily and reliably established.

BRIEF DESCRIPTION OF THE INVENTION

In accordance with the invention an ultrasonic handpiece is provided in which the work tip is to be replaced after a single use and there can be a quick and reliable provision of the aspiration and irrigation flow forces and fluids to the instrument. While the instrument is described using a magnetostrictive transducer, various features have application to hand pieces that use a piezo-electric transducer.

The ultrasonic instrument includes a generator of ultrasonic energy; a connecting body that receives ultrasonic energy from the generator and has an end from which the energy exits. A coupler is provided at such end having an aspiration flow passage for receiving aspiration flow force from a source to remove emulsified material from an operating site. A work tip has its proximal end connected to the coupler to receive the ultrasonic energy from the connecting body and a distal end from which the ultrasonic energy is to be supplied to the operating site to emulsify material. The work tip has an aspiration passage that is in communication with the coupler aspiration passage with at least one of the work tip being detachable from the coupler and coupler detachable from the connecting body or the work tip and coupler detachable as a unit.

In accordance with the invention, aspiration fluid flow force is provided through the coupler to the work tip aspiration passage without coming into contact with the interior of the connecting body. This permits removal of the work tip so that the instrument can be re-used by replacing the work tip and without sterilization of the connecting body.

In one form of the invention the coupler is a body that has a first, proximal, end connected to the end of the connecting body from which the ultrasonic energy exits and a second end to which the proximal end of the work tip is connected. The coupler body has an inlet passage to receive aspiration flow force, such as from a suction type pump, and an aspiration passage in communication therewith that also communicates with the work tip aspiration passage when the work tip is connected to the coupler. Preferably, a sleeve, that can be mounted to the connecting body or other part of the instrument, is spaced from and surrounds the coupler body and a portion of the work tip.

In one embodiment, there is a resilient sealing element between the exterior of the coupler body and the interior of the sleeve on each side of the coupler body inlet passage to define a first chamber between the sealing elements to which the aspiration fluid flow force is applied. Irrigation fluid also is supplied to the interior of the sleeve in the space between the resilient element closest to the work tip proximal end to pass in the space between the work tip exterior and the interior of the sleeve.

In another embodiment, the aspiration flow force is applied through a tube directly connected to the coupler body inlet passage. In this embodiment a sleeve also can be used and irrigation fluid supplied to a chamber formed between the interior of the sleeve and a single sealing element distal of the coupler body inlet passage.

In still a further embodiment of the invention there is a collar at the end of the connecting body from which the ultrasonic energy exits and a passage from the collar through the connecting body to the exterior of the connecting body. A flexile tube extends through the connecting body passage and has a first end exterior to the connecting body to receive the aspiration flow force and a second end having a part that opens into the collar. With the proximal end of the work tip fastened to the collar the work tip aspiration passage is in fluid flow communication with the tube to receive the aspiration fluid flow force that is applied to the work tip aspiration passage.

In all of the embodiments the aspiration flow force does not come into contact with any part of the connecting body. Thus, the work tip alone or the work tip and coupler body can be detached and disposed of and the instrument reused without sterilization by using a new work tip and coupler body. In the embodiment using the flexible tube passing through the connecting body, the work tip and tube are removed and replaced.

OBJECTS OF THE INVENTION

An object of the invention is to provide an ultrasonic instrument in which the work tip can be easily removed and no sterilization is needed for the connecting body.

A further object is to provide an ultrasonic instrument in which aspiration flow force used for removing emulsified tissue from the operating site does no come into contact with the connecting body.

Still a further object is to provide an ultrasonic instrument in which a coupler body is attached to the connecting body and aspiration flow force is provided through the coupler body to the work tip aspiration passage.

Yet another object is to provide aspiration flow force through a tube passing through the connecting body to a work tip that is coupled to the connecting body.

BRIEF DESCRIPTION OF THE DRAWINGS

Other objects and advantages of the present invention will become more apparent upon reference to following specification and annexed drawings in which:

FIG. 4 is a cross-sectional view of a third embodiment;

FIG. 5 is a view of a further embodiment; and

FIG. 5A is a view of a component used in the embodiment of FIG. 5.

DETAILED DESCRIPTION OF THE INVENTION

Figure 1:
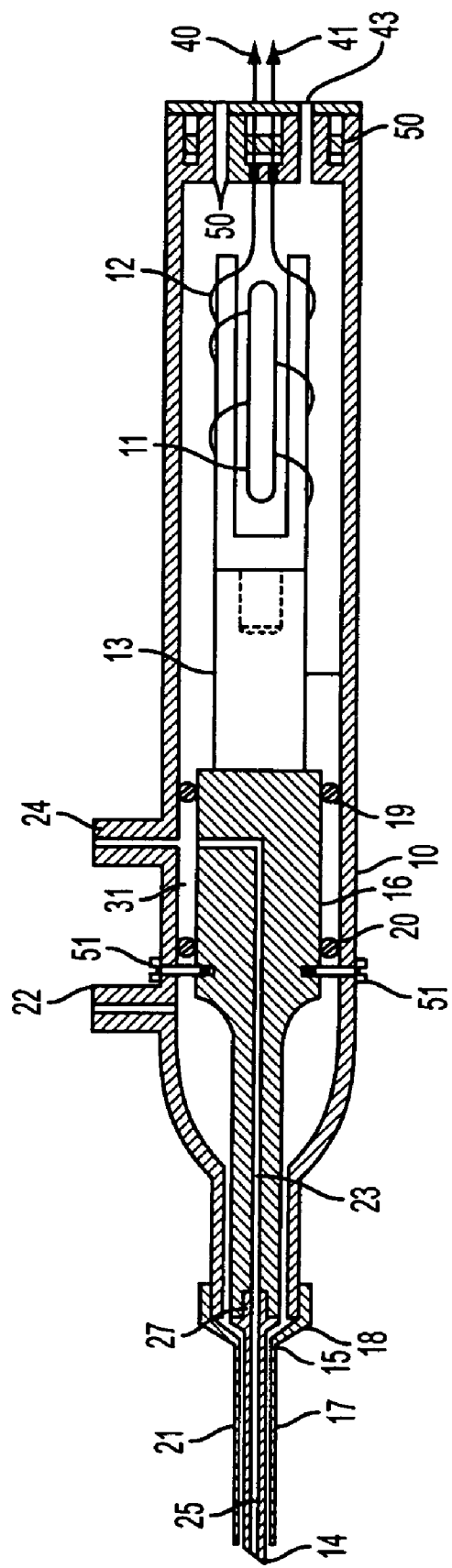
FIG. 1 is a cross-sectional view of a prior art ultrasonic instrument.

FIG. 1 depicts one type of prior art ultrasonic handpiece as shown in U.S. Pat. No. 4,504,264. There is a casing 10 of, for example, plastic or metal, within which is supported a transducer means 11 for generating mechanical vibrations upon excitation with an alternating-current electrical signal. The transducer 11 preferably is a magnetostrictive transducer with an electrical coil 12 wound about each leg of a stack of metal laminations so that longitudinal mechanical vibrations are produced. There is a connecting body 16 of, for example, titanium, having a reduced diameter distal end portion, which also can be an attached separate portion. The connecting body 16 forms an acoustic impedance transformer for conveying the longitudinal vibrations of the transducer 11 for application to an operative tool or working tip 14 connected to the distal end of the connecting body 16.

The work tip 14 distal end is at least partially external of the casing 10 and is supported thereby and is connected, such as by a screw thread 27, to the narrowed distal end of the connecting body 16 so as to be coupled to the transducer 11 to be longitudinally vibrated thereby. The working tip 14 is an elongated, hollow tip of a suitable metal, such as titanium, that is capable of supporting ultrasonic vibrations and has a distal end of a desired shape to be placed at an operating site against the tissue to be removed. The work tip 14 has a threaded proximal base portion 15 in engagement with the distal end of the connecting body 16 by a screw thread arrangement 27. The tip 14 can be interchanged by use of the screw threads.

The distal end of the tip 14 is shown surrounded by a sleeve 17, such as of silicone, whose proximal end is supported in threaded engagement on a reduced diameter end 18 with the casing 10. If desired, the proximal end of sleeve 17 can be engaged more proximally along the length of the casing 10 or mounted to the connecting body. The connecting body 16 has disposed thereon two elastomeric O-rings 19, 20 which provide fluid-tight seals between the connecting body 16 and the internal wall of casing 10. A plurality of screws 51 are shown disposed around the axis of the casing 10 for preventing longitudinal displacement (other than vibrational) or rotational movement of the vibratory structure within the casing and also for radially centering the vibratory structure within the casing. Other types of conventional mounting arrangements can be used.

The instrument also illustratively has electrical input terminals 40, 41 for applying a suitable electrical signal to the magnetostrictive transducer 11. A cooling water inlet 42 and a cooling water outlet 43 for circulating cooling water inside the casing 10 in the region around the magnetostrictive transducer 11 and connecting body 13 are provided and are sealed by an O-ring 19 and by a fluid-tight grommet 50.

The sleeve 17 around the tip 14 forms a first fluid passage 21 between the tip 14 and the sleeve for irrigation fluid and an inlet is provided on the casing or sleeve for supplying the irrigation fluid to the passage 21 from a supply of fluid (not shown) that is preferably sterile. There is a passage 23 formed through the connecting body 16 that is in communication with a central (aspiration) passage 25 of the work tip 14. An outlet 24 on the casing or sleeve receives a suction (aspiration) force that is applied to the passage 23 in the connecting body and the passage 25 in the work tip. A chamber 31 is formed between the spaced O-rings 19, 20 on the body 16 and the casing 10, or sleeve, with which the aspiration force communicates. Thus the aspiration force is from the source, into the chamber 31 between the O-rings, through the passage 23 in the connecting body and the passage 25 in the work tip 14. Tissue that is emulsified by the work tip is aspirated from the operating site by the aspiration flow force.

Other apparatus (not shown) for the instrument includes a suction pump, a treatment fluid supply, an oscillator for applying an electrical signal to the vibratory structure and control apparatus therefore. All of these are of conventional construction.

Considering now the operation of the instrument of FIG. 1, when an electrical signal having a frequency of, for example, 40,000 cycles is applied to the coil 12 around the magnetostrictive transducer 11, the transducer 11 vibrates longitudinally at 40,000 cycles per second, thereby vibrating the connecting bodies 13, 16 and the working tip 14. Treatment (irrigation) fluid is supplied through inlet 22 and fluid passage 21 to bathe the tissue in the operating site region around the working tip 14. Suction flow (aspiration) force is applied through inlet 24 and connecting body passage 23 to the working tip 14 aspiration passage 25 to withdraw the tissue fragmented (emulsified) by the work tip as it vibrates.

The instrument of FIG. 1 is not optimally adopted for single use of the work tip 14. While the work tip 14 can be separated for changing or sterilization by unthreading it from the narrowed distal end of the connecting body 16, a problem remains in that the portion of the aspiration passage 23 in the connecting body 16 still might not be sanitary. That is, a residue from a previous operation might remain in the aspiration passage 23. Therefore, at the very least, the connecting body 16 should be sterilized before another operation is performed using the instrument. This requires time and effort and might not be a convenient procedure to performed at a particular time.

Figure 2:
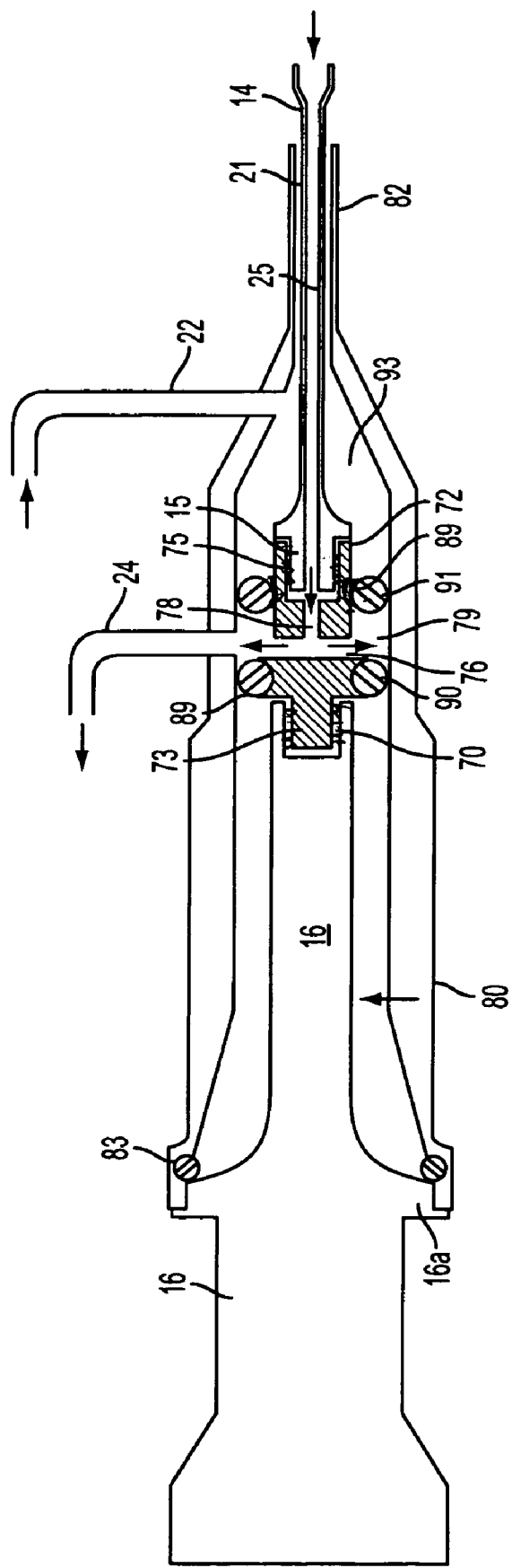
FIG. 2 is a cross-sectional view of a first embodiment of an ultrasonic instrument in accordance with the invention.

FIG. 2 shows a preferred embodiment of an ultrasonic surgical instrument according to the invention in which there is no aspiration fluid flow passage in the connecting body and the work tip 14 can be more easily changed. The same reference numerals are used for the same elements present in FIG. 1. Here the distal end portion of the connecting body 16 is tapered and has an internally threaded recess 70 at its end. A threaded collar can be used as an alternative. A coupler body 72 is provided externally of the connecting body 16 that has a threaded stud 73 at its proximal end to screw into the connecting body threaded recess 70 and a threaded recess 75 at its distal end into which the threaded base 15 of the work tip 14 is screwed. The coupler 72 is of a suitable material, such as the same metal as the connecting body 16 and is shown as a generally cylindrical body. If desired, the coupler body outer surface can have flats or grooves to accommodate a wrench, spanner or other tool.

Coupler 72 has a radial inlet aspiration flow force passage 76 between the stud 73 and recess 75. The passage 76 preferably extends across the diameter of the coupler body. There is a longitudinal passage 78 whose proximal end communicates with the radial passage 76 and whose distal end communicates with the aspiration passage 25 in work tip 14 when the work tip base 15 is threaded into the coupler recess 75.

The instrument of FIG. 2 has a sleeve 80 whose proximal end is connected to a flange 16a on the connecting body 16, such as by a threaded engagement or a snap-press fit with an O-ring 83 between the two members. Any other suitable type of connection can be used, such as mounting the sleeve to a case in which the instrument is mounted. All of this is conventional. The sleeve can be of any suitable material, such as a plastic. Sleeve 80 has a distal section 82 that surrounds, but is spaced from, the exterior of work tip 14 to establish the irrigation fluid flow passage 21.

The sleeve 80 has the aspiration force supply port 24 to which a suitable tubing (not shown) is to be connected to supply the force to remove the material from the operating site. Port 24 is positioned generally opposite the coupler radial passage 76. There are a pair of O-rings 90 and 91, one mounted on each side of the coupler radial passage 76, between the exterior of coupler body 72 and the interior of sleeve 80. If desired, circular grooves 89 can be formed on the outer surface of coupler 72 into which the O-rings 90, 91 can be fitted. Alternatively, grooves to hold the O-rings can be formed on the interior of the sleeve 80. The O-rings 90, 91 provide a fluid tight seal between the interior of sleeve 80 and the coupler 72 on each side of the coupler radial passage 76 and form a chamber 79. Thus, aspiration force supplied through the port 24 is applied to the work tip aspiration passage 25 and emulsified material removed through the chamber 79, coupler radial passage 76 and the transverse passage 78. The radial passage 76 illustratively is shown extending completely through the coupler so that there are two opposed entries into the chamber 79. This increases the flow force that can be applied to remove the emulsified material. The radial passage 76 can extend only part way through the coupler 72 and terminate at the transverse passage 78.

As seen, there is no communicating passage from the tip aspiration passage 25 to the connecting body 16 since the proximal end of the coupler 72 is solid. That is, the aspiration passage does not extend through the connecting body. If desired, the confecting body 16 can have a passage for cooling fluid.

An inlet port 22 for the irrigation fluid is provided on the sleeve 80 distally of the O-ring 91 and a chamber 93 is formed that communicates with the irrigation passage 21 surrounding the work tip 14. As seen, the irrigation fluid chamber 93 is sealed from the aspiration fluid chamber 79 by the O-ring 91. Irrigation fluid supplied through the port 22 to the chamber 93 flows through the tip irrigation passage 21 to the distal end of the tip 14 to be available at the operating site.

In the embodiment of FIG. 2, the work tip is replaced by first detaching the sleeve 80 from the connecting body and removing it. This leaves the tip 14 and coupler 72 exposed. The tip 14 can be unthreaded from the coupler 72 and the coupler then unthreaded from the connecting body 16. Preferably, the coupler 72 with the tip 14 attached is unthreaded from the connecting body 16. As indicated above, if the O-rings 90, 91 are in grooves on the coupler 72, then they would also be detached together with the coupler. The detached tip, and preferably also the coupler and O-rings, are then disposed of. It is also preferred that the sleeve 80 be disposed of since its interior forming the aspiration chamber 79 has been contacted by the material that was aspirated from the operating site. There is no need to perform any cleaning or sterilization for the connecting body 16.

Figure 3:
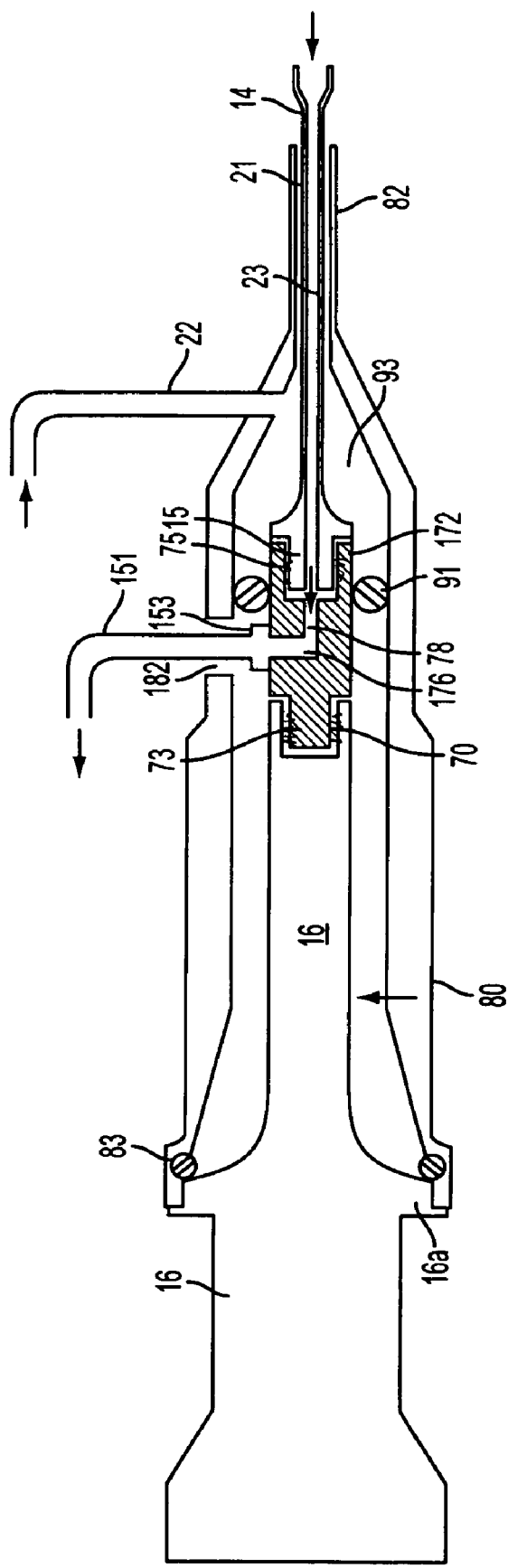
FIG. 3 is a second embodiment of the ultrasonic instrument of the invention.

FIG. 3 shows a further embodiment of the invention with a different type of coupler 172 in which the radial passage 176 extends only into the coupler for a distance sufficient to meet the transverse passage 78. The sleeve 80 has an opening 182 of sufficient size to provide access to the coupler radial passage 176. A flexible tube 151, such as of a plastic material, that supplies the aspiration flow force has one end connected to the aspiration flow source (not shown). The other end has a headed end 153 with a nipple of a deformable material, such as a soft plastic, that is inserted into the opening of the radial passage 176. The nipple of head 153 is press fit into the passage opening. If desired, a Leur or other suitable type of connector can be used to connect the tube 151 head 153 to the passage 176. A direct flow path is established between the aspiration fluid flow source and the work tip aspiration passage 23 trough the tube 151 and passages 176 and 76 in the coupler 72.

In this embodiment, the sleeve 80 is not necessary since no chamber has to be provided for the aspiration flow force. Use of a sleeve is preferred so that the O-ring 91 is used between the coupler and the sleeve to establish the irrigation fluid chamber 93 that communicates with the work tip irrigation fluid passage 21.

The tip is removed in the manner described above with respect to FIG. 2 by first removing the sleeve 80 and then unthreading the tip from the coupler or, preferably by unthreading the coupler with the tip attached from the connecting body 16. In this embodiment the aspirated material does not come into contact with the interior of sleeve 80 so that it is not necessary to dispose of the sleeve.

FIG. 4 shows a modification of the coupler of FIG. 3. Here a duct 181, such as a piece of tubing of a suitable material compatible with the coupler 172 is affixed to and extends outwardly from the coupler 172. The duct 181 is accessible through the opening 182 in the sleeve 80, if such sleeve is used. The flexible tube 151 has an enlarged reinforced head 183 that is fitted over the duct 181. Aspiration flow force is provided to the aspiration passage 23 in the work tip 14 through the duct 181 and coupler passages 176 and 78. The tip 14 is removed from the instrument in the same manner as described with respect to the embodiment of FIG. 3.

While the couplers 72 and 172 of FIGS. 2–4 are shown as being separate from the work tip 14, it should be understood that they can be made integral with the proximal end of the tip so that the tip and coupler can be removed as a unit.

FIGS. 5 and 5A show another embodiment of the coupler that permits removal of the work tip. Here a threaded collar 191 is formed on the exterior of the narrowed distal end of the connecting body 16 to accept the threaded base 15 of the work tip 14. A passage 205 is formed through the connecting body 16 that has one end 207 on the outer surface of the body 16 and a second end 208 that opens in the collar 191 opposite the entry to the aspiration passage 23 in the tip 14. A flexible tube 201 of plastic material is provided that is of a diameter smaller than the connecting body passage 205 and has a washer, or flange, type head 203.

In use, the free end of tube 201 is passed into the collar 191 and through the end 208 of the connecting body passage 205 to exit from the body passage 207. The washer type head 203 is pressed against the back end of the collar 191 against the connecting body. The free end of the tube 201 remote from the washer head 203 is connected to the aspiration flow source by any suitable type of connecting arrangement. When the base end 15 of tip 14 is threaded into the collar 191, a seal relative to the tube 201 is formed with the washer head 203. There is communication between the aspiration fluid flow source and the work tip aspiration passage 25 through the tube 201. The sleeve 80 for the irrigation fluid is not shown but it can be as in FIG. 4.

In use, the work tip 14 can be unthreaded from the collar 191 and disposed of. The tube 201 is then pulled out of the connecting body passage 205 and disposed of. The free end of the tube 201 can be sealed before the tube is pulled out of the connecting body passage so that there is no leakage of material from the tube as it is pulled from the body. Here also there is no contact of material removed from the operating site with any part of the connecting body 16. Therefore, the connecting body does not have to be sterilized.

While threaded connections have been shown between the work tip and the connecting body, it should be understood that other types of connections, such as a bayonet lock can be used.

Specific features of the invention are shown in one or more of the drawings for convenience only, as each feature may be combined with other features in accordance with the invention. Alternative embodiments will be recognized by those skilled in the art and are intended to be included within the scope of the claims.

We claim:

1. An ultrasonic instrument comprising:
   a generator that receives electrical energy and converts the electrical energy into mechanical vibrations of ultrasonic energy;
   a connecting body having a second end connected to said generator to receive the mechanical vibrations of ultrasonic energy from said generator and convey the vibrations to a first end from which the vibrational energy exits, said connecting body having no internal fluid flow passage;
   a separable coupler threadably, detachably connected to and external of said connecting body first end, said coupler comprising a body having a first end detachably connected to said connecting body first end and a second end to which a work tip proximal end is to be connected, the ultrasonic vibrations being conveyed from said coupler body first end to said coupler body second end, said coupler body also having an internal aspiration fluid flow passage with an inlet at said coupler body second end, and an outlet for said coupler aspiration flow passage that is at the exterior of said connecting body and between said coupler body first and second ends in fluid communication with said coupler body internal aspiration fluid flow passage for receiving aspiration flow force from a source that flows through said aspiration fluid flow passage to remove emulsified material from an operating site; and
   a work tip having a proximal end connected to said coupler body second end to receive the ultrasonic vibrational energy and a distal end from which the ultrasonic energy is supplied to the operating site to emulsify material, said work tip having an aspiration fluid flow passage that is in communication with said coupler body aspiration fluid flow passage inlet at said coupler body second end, wherein said coupler and said work tip are both detachable from said connecting body first end while leaving said connecting body attached to said generator.

2. An ultrasonic instrument as in claim 1 further comprising:
   an inlet conduit having a first end for direct connection to said inlet of said coupler aspiration flow passage to supply the aspiration flow force to said coupler aspiration flow passage and a second end for receiving the aspiration flow force.

3. An ultrasonic instrument as in claim 2 further comprising:
   a sleeve spaced from and surrounding said coupler and a portion of said work tip, said sleeve having an opening to provide access of said conduit first end to said inlet of said coupler aspiration flow passage; and
   a first sealing element between the exterior of said coupler and the interior of said sleeve distally of said inlet of said coupler aspiration flow passage to define a chamber to receive irrigation fluid to flow in the space between the interior of said sleeve and the portion of said work tip surrounded by said sleeve.

4. An ultrasonic instrument as in claim 3 further comprising a groove on the exterior of said coupler body in which said first sealing element fits.

5. An ultrasonic instrument as in claim 2 wherein said one end of said conduit includes a piece that is inserted into said inlet of said coupler aspiration flow passage.

6. An ultrasonic instrument as in claim 2 further comprising a duct extending from said coupler in communication with said inlet of said coupler aspiration flow passage and said conduit first end is connected to said duct.

7. An ultrasonic instrument as in claim 1 further comprising:
   a sleeve spaced from and surrounding said coupler and a portion of said work tip;
   first and second sealing elements between the exterior of said coupler and the interior of said sleeve respectively positioned on each side of said inlet of said aspiration flow passage to define a first chamber between said first and second sealing elements with said coupler inlet of said aspiration flow passage being in fluid flow communication with said first chamber; and wherein said sleeve has an inlet port to supply the aspiration flow force to said first chamber.

8. An ultrasonic instrument as in claim 7 wherein said coupler has a plurality of inlets to provide a plurality of inlets from said first chamber to said coupler aspiration flow passage.

9. An ultrasonic instrument as in claim 7 further comprising an inlet on said sleeve distally of said first chamber to provide irrigation fluid to the interior of said sleeve to flow between the exterior of said work tip end the interior of said portion of said sleeve that surrounds said work tip.

10. An ultrasonic instrument as in claim 7 further comprising a respective groove on the exterior of said coupler body in which each said first and second said resilient element fits.

11. An ultrasonic instrument as in claim 1 wherein said proximal end of said work tip is threaded into said coupler second end.

12. An ultrasonic instrument as in claim 1 wherein said coupler and said work tip are detachable from said connecting body as a unit.

\* \* \* \* \*